United States Patent [19]

Briner

[11] Patent Number: 5,169,993
[45] Date of Patent: Dec. 8, 1992

[54] CYCLOHEXENOL DERIVATIVES

[75] Inventor: Paul H. Briner, Canterbury, England

[73] Assignee: Shell Research Limited, United Kingdom

[21] Appl. No.: 746,975

[22] Filed: Aug. 19, 1991

[30] Foreign Application Priority Data

Sep. 3, 1990 [GB] United Kingdom ............... 9019195

[51] Int. Cl.$^5$ .................. C07C 33/38; C07C 33/50; C07C 35/21
[52] U.S. Cl. .................................. 568/807; 568/812; 568/819; 568/822; 568/832; 568/835
[58] Field of Search ............ 568/819, 704, 823, 825, 568/832, 835, 631, 636, 637, 812, 807; 558/423; 564/57, 152, 339; 562/468

[56] References Cited

PUBLICATIONS

Clarembeau et al. "Tetrahedron Letters", vol. 26, No. 8, pp. 1093–1096 (1985).
Clarembeau et al, "Chem. Abstracts" vol. 103:142047q (1985).
Zoeckler et "J. American Chem. Soc." vol. 103, pp. 7661–7663 (1981).
Zoeckler et al "Chem. Abst." vol. 96;19428z (1982).

*Primary Examiner*—Werren B. Lone

[57] ABSTRACT

The invention provides cyclohexenol derivatives of the general formula

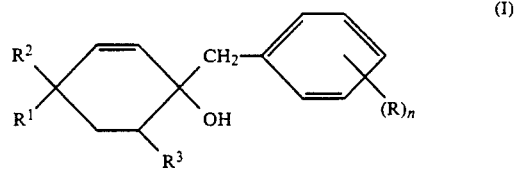

(I)

in which n represents an integer from 0 to 5; each R represents a halogen atom, nitro, cyano, hydroxyl, alkyl, haloalkyl, alkoxy, haloalkoxy, amino, alkylamino, dialkylamino, alkoxycarbonyl, carboxyl, alkanoyl, alkylthio, alkylsulphinyl, alkylsulphonyl, carbamoyl, alkylamido, cycloalkyl or phenyl group; and $R^1$, $R^2$ and $R^3$ independently represent a hydrogen atom or an alkyl group, with the provisos that when $R^1$, $R^2$ and $R^3$ all represent a hydrogen atom then n is not 0 and, when $R^1$, $R^2$ and $R^3$ all represent a hydrogen atom and n is 1, R does not represent a fluorine atom substituted at the 4-position of the phenyl ring; and a process for their preparation. Compounds of formula I are useful as intermediates in the preparation of certain fungicidal active cyclopentane derivatives.

2 Claims, No Drawings

CYCLOHEXENOL DERIVATIVES

This invention relates to certain cyclohexenol derivatives, which are useful as intermediates in the preparation of fungicidally active cyclopentane derivatives, and a process for their preparation.

Tetrahedron Letters, 26, No. 8, pp 1093–1096, (1985) discloses 1-benzylcyclohex-2-en-1-ol and 1-(4-fluorobenzyl)cyclohex-2-en-1-ol.

It has now been discovered that certain cyclohexenol derivatives are useful as intermediates in a highly stereospecific route to certain fungicidally active cyclopentane derivatives.

According to the present invention there is therefore provided a compound of the general formula

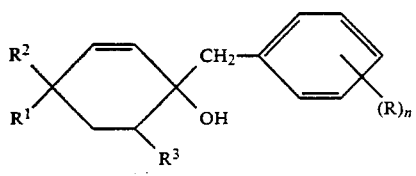

(I)

in which n represents an integer from 0 to 5; each R represents a halogen atom, nitro, cyano, hydroxyl, alkyl, haloalkyl, alkoxy, haloalkoxy, amino, alkylamino, dialkylamino, alkoxycarbonyl, carboxyl, alkanoyl, alkylthio, alkylsulphinyl, alkylsulphonyl, carbamoyl, alkylamido, cycloalkyl or phenyl group; and $R^1$, $R^2$ and $R^3$ independently represent a hydrogen atom or an alkyl group; with the provisos that when $R^1$, $R^2$ and $R^3$ all represent a hydrogen atom then n is not 0 and, when $R^1$, $R^2$ and $R^3$ all represent a hydrogen atom and n is 1, R does not represent a fluorine atom substituted at the 4-position of the phenyl ring.

When any of the foregoing substituents represents or contains an alkyl substituent group, this may be linear or branched and may contain up to 12, preferably up to 6, and especially up to 4, carbon atoms. A cycloalkyl substituent group may contain 3 to 8, preferably 3 to 6, carbon atoms.

It is preferred that $R^1$, $R^2$ and $R^3$ independently represent a hydrogen atom or a $C_{1-4}$ alkyl, particularly a methyl, group.

Preferably, R represents a halogen, especially a chlorine atom.

A particularly preferred sub-group of compounds of formula I is that in which n is 1, R represents a chlorine atom, preferably substituted at the 4-position of the phenyl ring, $R^1$ and $R^2$ both represent a hydrogen atom or both represent a methyl group and $R^3$ represents a hydrogen atom or methyl group.

The present invention also provides a process for the preparation of a compound of formula I as defined above which comprises reacting a compound of the general formula

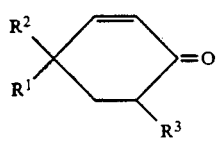

(II)

in which $R^1$, $R^2$ and $R^3$ are as defined above, with a compound of the general formula

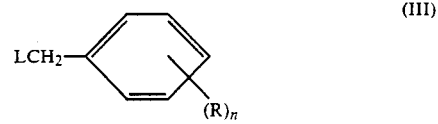

(III)

in which R and n are as defined above and L represents an organometallic group. Suitable organometallic groups include lithium and the group —MgHal where Hal represents a chlorine or bromine atom.

The process is conveniently carried out in the presence of a solvent. Suitable solvents include ethers, such as diethyl ether and methyl t-butyl ether.

The reaction is suitably carried out at a temperature in the range from 0° C. to the reflux temperature of the solvent, if present.

Compounds of formula II and III are known compounds or can be prepared by processes analogous to known processes.

The compounds of formula I are useful as intermediates in the preparation of fungicidally active cyclopentane derivatives of the general formula

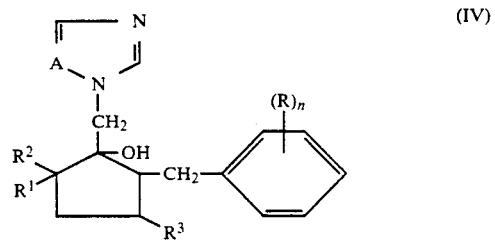

(IV)

in which n, R, $R^1$, $R^2$ and $R^3$ are as defined above and A represents a nitrogen atom or a CH group. Certain compounds of formula IV are the subject of co-pending patent applications GB-A1-2180236 and EP-A2-0267778. The compounds disclosed in EP-A2-0267778 and GB-A1-2180236 exist in two stereoisomeric forms which have the following structures:

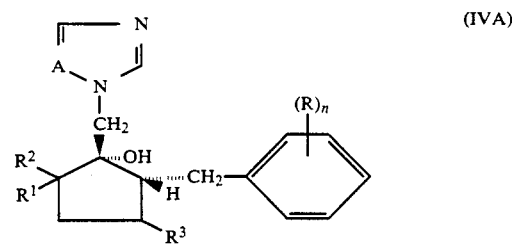

(IVA)

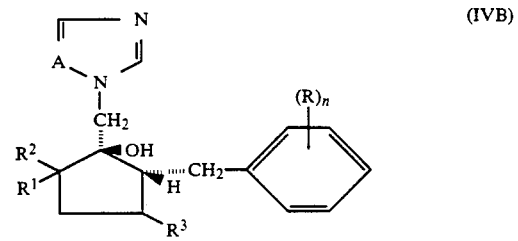

(IVB)

The letters A and B will be used hereinafter to denote compounds having the same stereochemical configuration as isomers A and B above.

Isomers A and B can be separated by, for instance, chromatography and exhibit different fungicidal activity. Generally, isomers of formula IVA exhibit greater fungicidal activity than isomers of formula IVB. The process used to synthesise compounds of formula IVA from compounds of formula I is set out in the following reaction scheme:

groups, $R^5$ represents a hydrogen atom or an alkyl, preferably a $C_{1-6}$alkyl, or cycloalkyl group, X represents a halogen, preferably a chlorine or bromine, atom, M represents an alkali metal, preferably a sodium or potassium, atom and Q represents a hydrogen or alkali metal, preferably sodium or potassium, atom. The intermediate compounds and process steps in the above

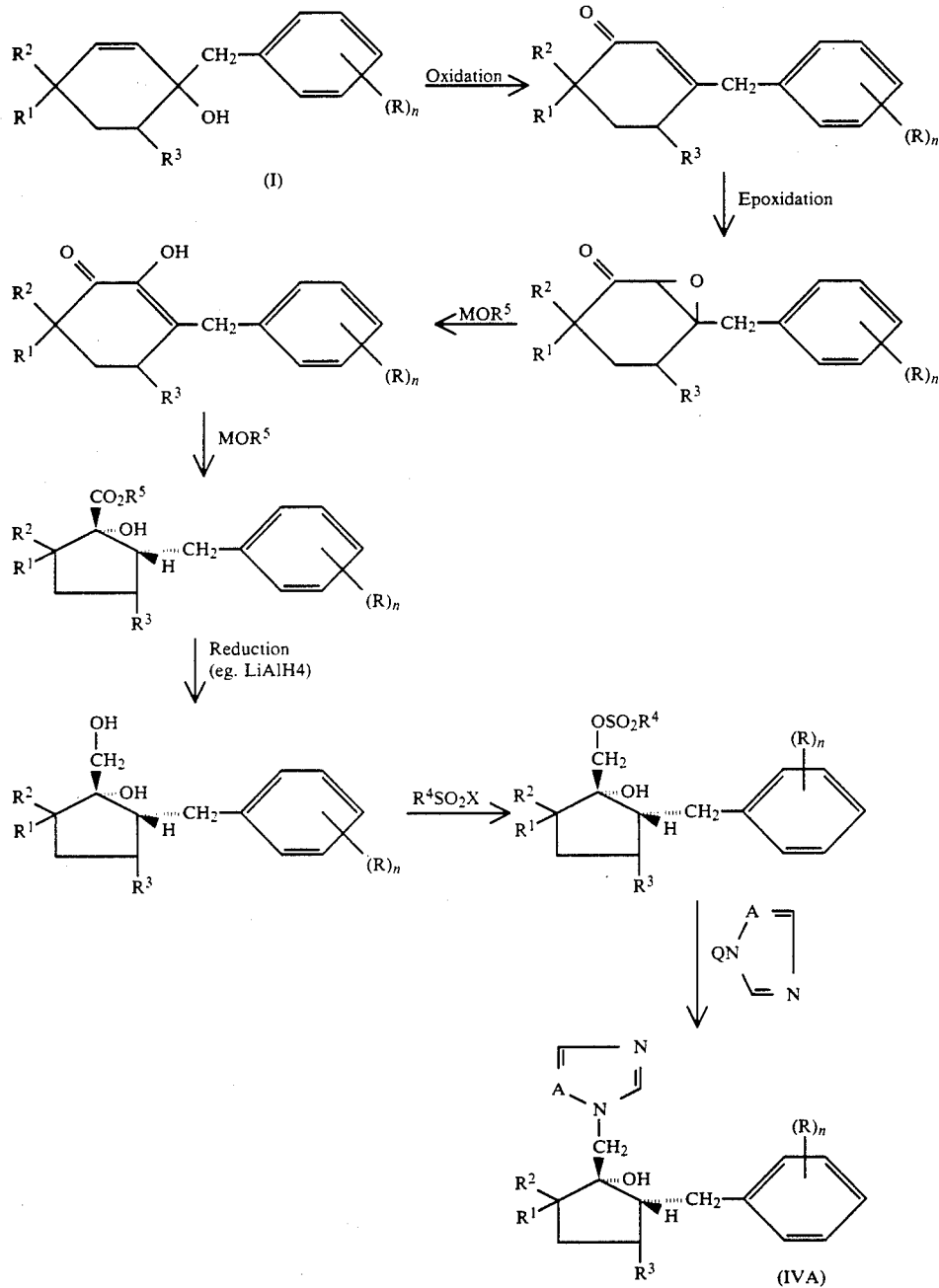

In the above reaction scheme, n, R, $R^1$, $R^2$, $R^3$ and A are as previously defined, R4 represents an optionally substituted alkyl or aryl group, preferably a $C_{1-4}$alkyl or a phenyl group each optionally substituted by one or more substituents selected from halogen atoms, nitro, cyano, hydroxyl, $C_{1-4}$alkyl, $C_{1-4}$haloalkyl, $C_{1-4}$alkoxy, $C_{1-4}$haloalkoxy, amino, $C_{1-4}$alkylamino, di-$C_{1-4}$alkylamino, $C_{1-4}$alkoxycarbonyl, carboxyl, $C_{1-4}$alkanoyl, $C_{1-4}$alkylthio, $C_{1-4}$alkylsulphinyl, $C_{1-4}$alkylsulphonyl, carbamoyl, $C_{1-4}$alkylamido, $C_{3-8}$cycloalkyl and phenyl reaction scheme are the subject of copending patent applications T 690 and T 693, copending European patent application no. 89202159.3 and copending British patent application no. 8820607.3.

The invention is further illustrated by the following Examples.

EXAMPLE 1

Preparation of
1-(4-Chlorobenzyl)-4,4-dimethylcyclohex-2-en-1-ol
(n=1, R=4—Cl, $R^1$=$R^2$=$CH_3$, $R^3$=H)

A solution of 4-chlorobenzyl chloride (266 g, 1.65 mol) in diethyl ether (200 ml) was added slowly to a stirred mixture of magnesium (42 g, 1.7 mol) in diethyl ether (700 ml) to maintain the mixture at reflux. The mixture was warmed for a further 20 minutes after addition was complete. A solution of 4,4-dimethylcyclohex-2-en-1-one (226 g, 1.82 mol) in diethyl ether (60 ml) was then added dropwise over a period of 30 minutes so as to maintain the mixture at reflux and the mixture stirred overnight. The mixture was then quenched with water (250 ml) and hydrochloric acid (5M, 500 ml), extracted with diethyl ether (3×400 ml), backwashed once with sodium bicarbonate solution (5% w/v) and once with water and then dried with anhydrous magnesium sulphate. The solvent was then flashed off to give 369 g 1-(4-chlorobenzyl)-4,4-dimethylcyclohex-2-en-1-ol as an oil.

NMR (in $CDCl_3$ solvent, tetramethylsilane as reference) Characteristic peaks at: δ(ppm): 0.90, 0.99 (3 H, singlet), 2.78 (2 H, singlet), 5.40 (1 H, doublet, J=11 Hz), 5.50 (1 H, doublet, J=11 Hz), 7.17 (2 H, doublet, J=8 Hz), 7.26 (2 H, doublet, J=8 Hz).

EXAMPLE 2

Preparation of
1-(4-Chlorobenzyl)-4,4,6-trimethylcyclohex-2-en-1-ol
(n=1, R=4—Cl, $R^1$=$R^2$=$R^3$=$CH_3$)

To a slurry of magnesium turnings (66 g, 2.73 g.atoms) in diethyl ether (300 ml) was added a solution of 4-chlorobenzyl chloride (418 g, 2.6 moles) in diethyl ether (1500 ml) at such a rate as to maintain gentle reflux. After a further 30 minutes, a solution of 4,4,6-trimethylcyclohex-2-en-1-one (340 g, 2.46 moles) in diethyl ether (350 ml) was added, again maintaining a gentle reflux. After 1 hour the mixture was added into saturated aqueous ammonium chloride (4 liters) and the phases separated. The ether phase was back-washed with water (1 liter) and used directly in the next reaction. A small portion of 1-(4-chlorobenzyl)-4,4,6-trimethylcyclohex-2-en-1-ol was isolated for characterisation (gas chromatography analysis showed two isomers in approximately equal amounts).

NMR (in $CDCl_3$ solvent, tetramethylsilane as reference). Characteristics peak at: δ(ppm): 0.75, 0.95, 1.00, 1.02, 1.05, 1.07, 1.09 (total 9 H), 2.00 (1 H, multiplet), 2.57, 2.79 (2 H, AB, J=12 Hz), 2.69, 2.94 (2 H, AB, J=12 Hz), 4.94 (1 H, doublet, J=10 Hz), 5.34 (1 H, doublet, J=10 Hz), 7.1-7.4 (4 H).

I claim:

1. The compound 1-(4-chlorobenzyl)-4,4-dimethylcyclohex-2-en-1-ol.
2. The compound 1-(4-chlorobenzyl)-4,4,6-trimethylcyclohex-2-en-1-ol.

* * * * *